(12) United States Patent
Ichikawa et al.

(10) Patent No.: US 8,445,654 B2
(45) Date of Patent: *May 21, 2013

(54) ANTIBIOTIC MACROCYCLE COMPOUNDS AND METHODS OF MANUFACTURE AND USE THEREOF

(75) Inventors: Yoshi Ichikawa, San Diego, CA (US); Yu-Hung Chiu, San Diego, CA (US); Youe-Kong Shue, Carlsbad, CA (US); Farah Kondori Babakhani, San Diego, CA (US)

(73) Assignee: Optimer Pharmaceuticals, Inc., Jersey City, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/280,148

(22) Filed: Oct. 24, 2011

(65) Prior Publication Data

US 2012/0040922 A1    Feb. 16, 2012

Related U.S. Application Data

(63) Continuation of application No. 12/324,907, filed on Nov. 28, 2008, now Pat. No. 8,044,030.

(60) Provisional application No. 60/996,609, filed on Nov. 27, 2007.

(51) Int. Cl.
*C07H 17/08* (2006.01)

(52) U.S. Cl.
USPC .......................................................... 536/7.1

(58) Field of Classification Search
USPC .......................................................... 536/7.1
See application file for complete search history.

(56) References Cited

U.S. PATENT DOCUMENTS 4,918,174 A * 4/1990 McAlpine et al. ............. 536/7.1

FOREIGN PATENT DOCUMENTS

WO    WO 2005/112990 A2 * 12/2005

* cited by examiner

*Primary Examiner* — Elli Peselev
(74) *Attorney, Agent, or Firm* — Morgan, Lewis & Bockius LLP

(57) ABSTRACT

The invention encompasses an active metabolite of the 18-membered macrocyclic antimicrobial agents, specifically, a metabolite of tiacumicin B and in certain embodiments, R-Tiacumicin B or and its related compounds. In particular, the invention encompasses a compound that acts as a potent antibiotic agent for the treatment of bacterial infections, specifically GI infections caused by toxin producing strains of *Clostridium difficile* (*C. difficile*) and *Clostridium perfringens* (*C. perfringens*).

8 Claims, 1 Drawing Sheet

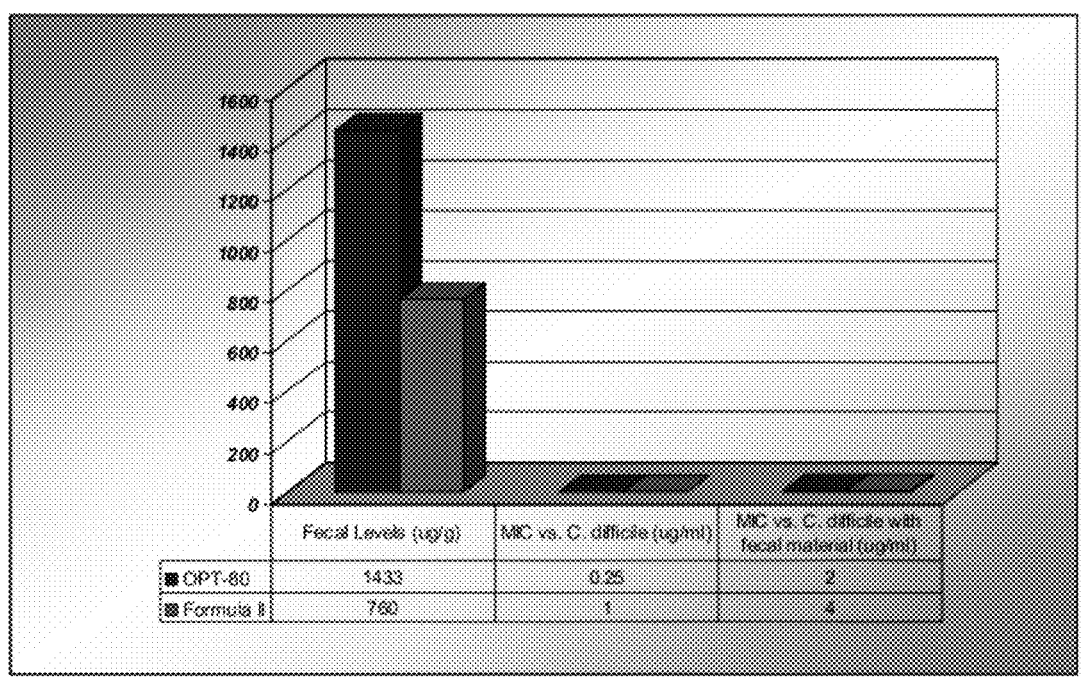
Comparison of OPT-80 and FORMULA II fecal levels with MIC values in the presence and absence of 5% fecal matter vs. *C. difficile* ATCC 700058

ANTIBIOTIC MACROCYCLE COMPOUNDS AND METHODS OF MANUFACTURE AND USE THEREOF

CROSS-REFERENCE TO RELATED APPLICATIONS

This application is a continuation application of U.S. application Ser. No. 12/324,907 filed Nov. 28, 2008, now U.S. Pat. No. 8,044,030 granted on Octber 25, 2011, which claims the benefit of U.S. provisional patent application No. 60/996,609, filed Nov. 27, 2007, all of which are herein incorporated herein by reference in their entireties.

FIELD OF THE INVENTION

The invention encompasses an active metabolite of the 18-membered macrocyclic antimicrobial agents, specifically, a metabolite of tiacumicin B and in certain embodiments, R-Tiacumicin B or and its related compounds. In particular, the invention encompasses a compound that acts as a potent antibiotic agent for the treatment of bacterial infections, specifically GI infections caused by toxin producing strains of *Clostridium difficile* (*C. difficile*) and *Clostridium perfringens* (*C. perfringens*).

BACKGROUND OF THE INVENTION

Macrocycles are an important therapeutic class of antibiotics. These compounds are frequently produced as a family of closely related biogenetic congeners. The Tiacumicins are a series of 18-membered macrocyclic antibiotics in which the macrocyclic ring is glycosidically attached to one or two sugars. As shown in Table 1, a seven-carbon sugar ($R^1$) is esterified at various positions with small fatty acids. The other sugar ($R^2$), when present, is esterified with an isomer of substituted benzoic acid such as everninic acid (*Journal of Liquid Chromatography*, 1988, 11: 191-201).

Tiacumicins are a family of related compounds that contain the 18-membered ring shown in Formula I below.

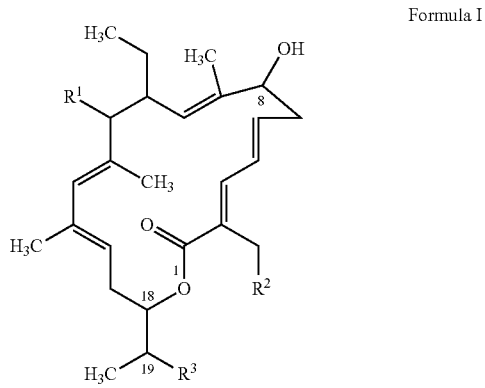

Formula I

At present, several distinct Tiacumicins have been identified and six of these (Tiacumicin A-F) are defined by their particular pattern of substituents $R^1$, $R^2$, and $R^3$ (See, e.g., U.S. Pat. No. 4,918,174; *J. Antibiotics*, 1987, 40: 575-588), as shown in Table 1.

TABLE 1

Substituents Present In Tiacumicins A-F

| | $R^1$ | $R^2$ | $R^3$ |
|---|---|---|---|
| A | [structure] | H | H |
| B | [structure] | [structure] | OH |
| C | [structure] | [structure] | OH |

TABLE 1-continued
Substituents Present In Tiacumcins A-F
| | R¹ | R² | R³ |
|---|---|---|---|
| D | | | OH |
| E | | | OH |
| F | | | OH |
More recently, a group of related substances were discovered and described in the U.S. patent application publication number US2007-105791 and include the following.
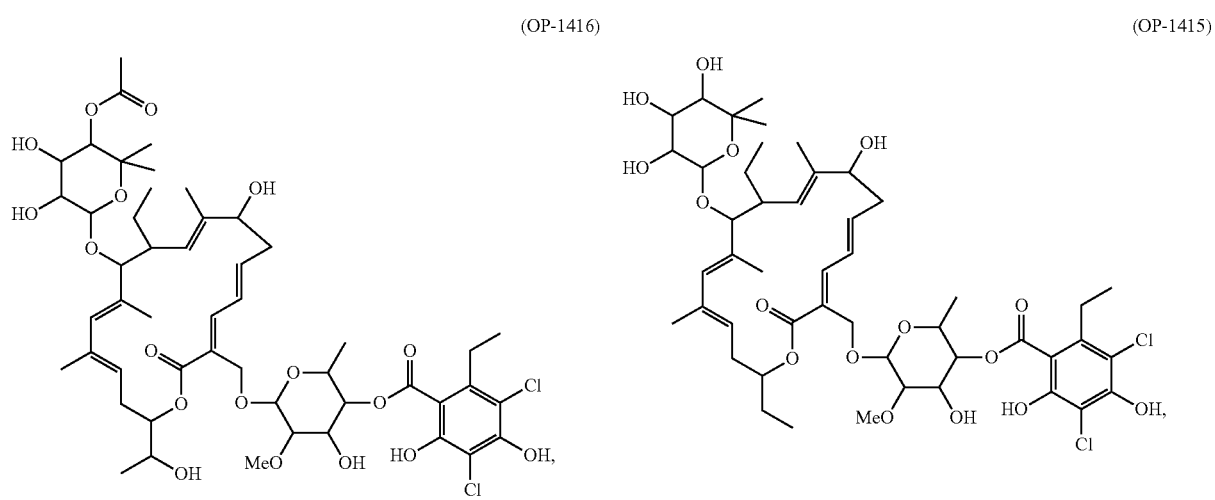
(OP-1416)  (OP-1415)

-continued
(OP-1417)
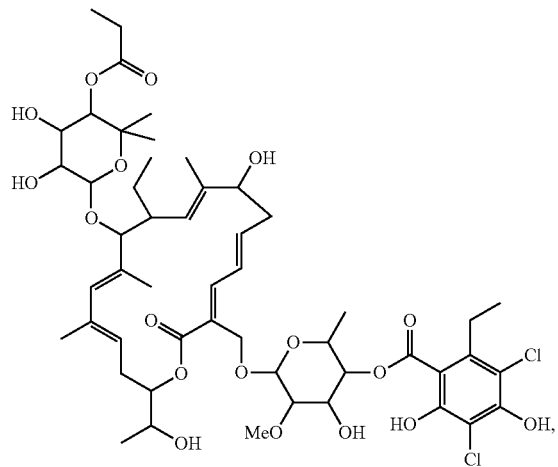
(OP-1435)
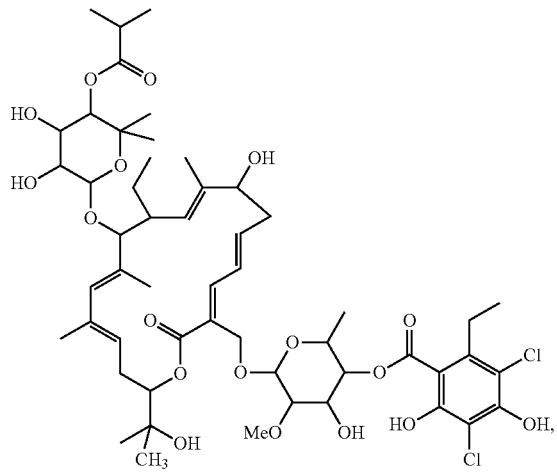
(OP-1437)
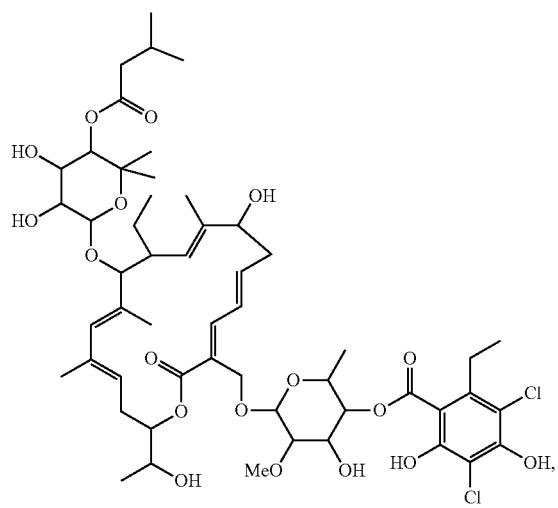
(OP-1402)
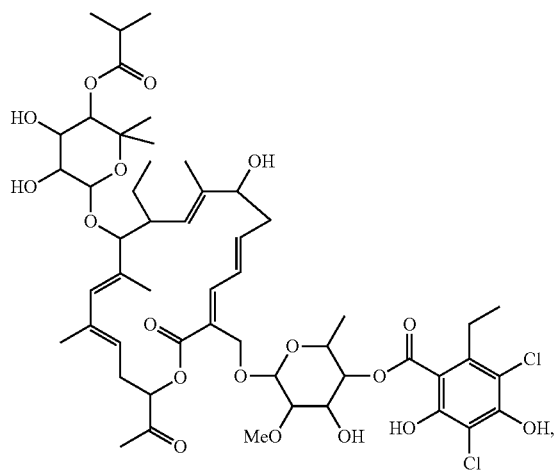
(OP-1433)
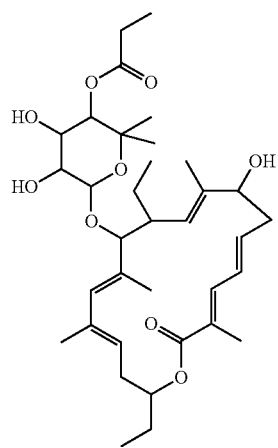
(OP-1438)
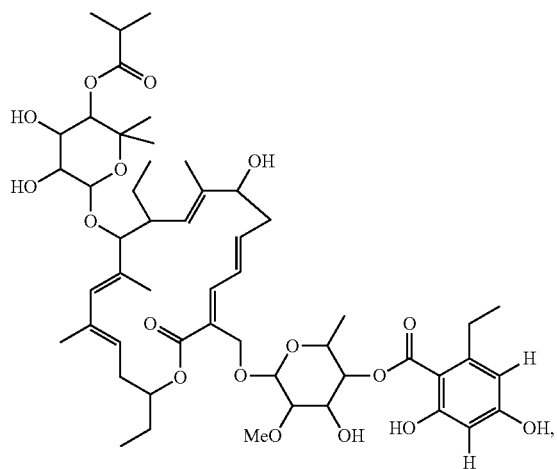

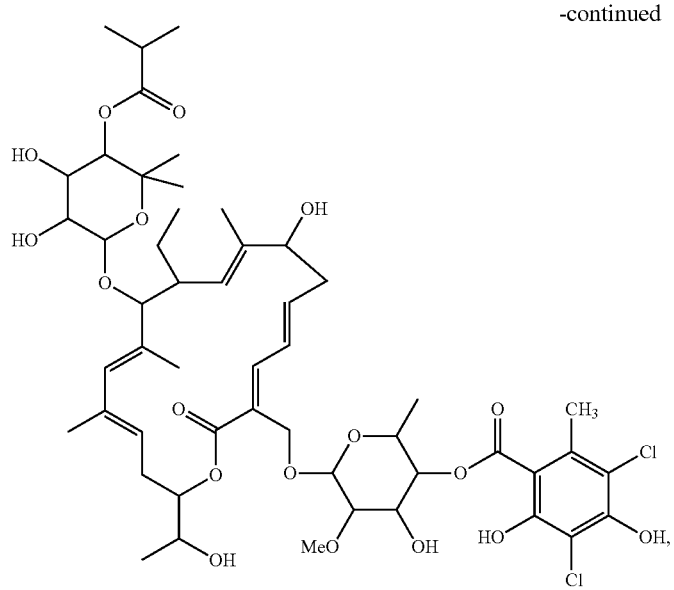

(OP-1405, Lipiarmycin A4)

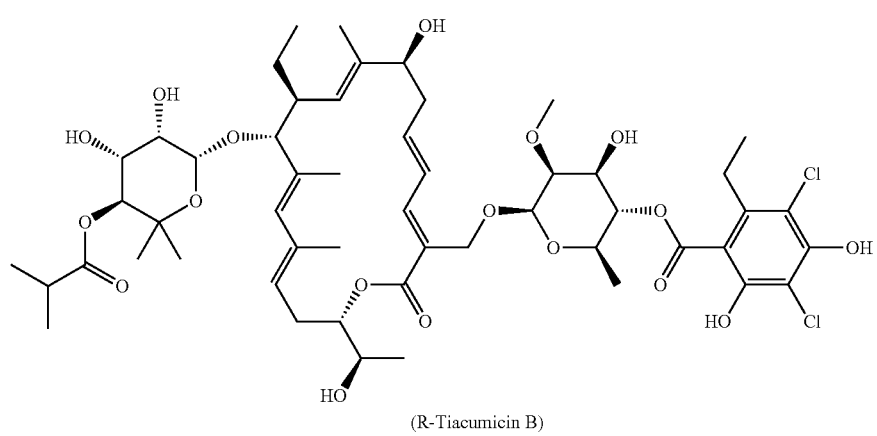

(R-Tiacumicin B)

Tiacumicins can be produced by bacteria, including *Dactylosporangium aurantiacum* subspecies *hamdenensis*, which may be obtained from the ARS Patent Collection of the Northern Regional Research Center, United States Department of Agriculture, 1815 North University Street, Peoria, Ill. 61604, accession number NRRL 18085. The characteristics of strain AB 718C-41 are given in *J. Antibiotics*, 1987, 40: 567-574 and U.S. Pat. No. 4,918,174.

Tiacumicins show activity against a variety of bacterial pathogens and in particular against *C. difficile*, a Gram-positive bacterium (*Antimicrob. Agents Chemother.* 1991, 1108-1111). *C. difficile* is an anaerobic spore-forming bacterium that causes an infection of the bowel. Diarrhea is the most common symptom but abdominal pain and fever may also occur. *C. difficile* is a major causative agent of colitis (i.e., inflammation of the colon) and diarrhea that may occur following antibiotic intake. This bacterium is primarily acquired in hospitals and chronic care facilities. Because Tiacumicin B shows promising activity against *C. difficile*, it is expected to be useful in the treatment of bacterial infections, especially those of the gastrointestinal tract, in mammals. Examples of such treatments include but are not limited to treatment of colitis and treatment of irritable bowel syndrome. Tiacumicins may also find use for the treatment of gastrointestinal cancers.

Tiacumicin antibiotics are described in U.S. Pat. No. 4,918, 174 (issued Apr. 17, 1990), *J. Antibiotics*, 1987, 40: 575-588, *J Antibiotics*, 1987, 40: 567-574, *J. Liquid Chromatography*, 1988, 11: 191-201, *Antimicrobial Agents and Chemotherapy* 1991, 35: 1108-1111, U.S. Pat. No. 5,583,115 (issued Dec. 10, 1996), and U.S. Pat. No. 5,767,096 (issued Jun. 16, 1998), which are all incorporated herein by reference. Related compounds are the Lipiarmycin antibiotics (c.f., *J. Chem. Soc. Perkin Trans. I*, 1987, 1353-1359 and *J. Antibiotics* 1988, 41: 308-315) and the Clostomicin antibiotics (*J. Antibiotics* 1986, 39: 1407-1412), which are all incorporated herein by reference.

SUMMARY OF THIS INVENTION

The invention encompasses a compound of Formula II:

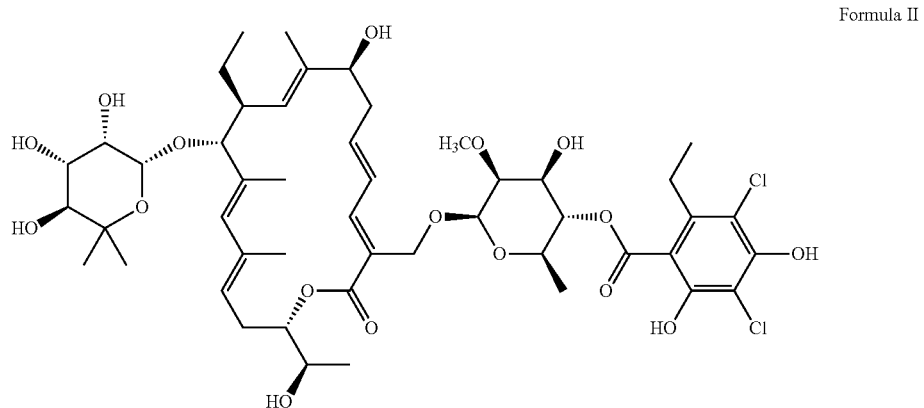 [SMILES: CCc1c(Cl)c(O)c(Cl)c(O)c1C(=O)O[C@H]1[C@H](O)[C@H](OC)[C@H](OC/C2=C\C=C\C[C@H](O)/C(C)=C/[C@H](CC)[C@@H](O[C@@H]3OC(C)(C)[C@@H](O)[C@H](O)[C@@H]3O)/C(C)=C/C(C)=C/C[C@@H]([C@@H](C)O)OC2=O)O[C@@H]1C]

Formula II in free form or a pharmaceutically acceptable salt thereof.

In other embodiments, the invention encompasses compositions including a compound of Formula II in free form or a pharmaceutically acceptable salt thereof. In certain embodiments, the invention encompasses compositions including a therapeutically effective amount of a compound of Formula II in free form or a pharmaceutically acceptable salt thereof. In certain other embodiments, the compositions further include a pharmaceutically acceptable carrier or excipient.

In another embodiment, the invention encompasses methods of treating diseases and/or disorders, for example, infections, for example, bacterial infections caused by gram-positive anaerobes, by administering to a subject in need thereof a therapeutically effective amount of a composition including a compound of Formula II in free form or a pharmaceutically acceptable salt thereof.

In still other embodiments, the invention encompasses methods of treating diseases and/or disorders, for example, infections, for example, bacterial infections caused by gram-positive anaerobes, by contacting a subject with an effective amount of a compound of Formula II in free form or a pharmaceutically acceptable salt thereof.

BRIEF DESCRIPTION OF THE FIGURES

FIG. 1 shows the Comparison of OPT-80 and Formula II fecal levels with MIC values in the presence and absence of 5% fecal matter vs. *C. difficile* ATCC 700058.

DETAILED DESCRIPTION OF THE INVENTION

General Description

The invention generally encompasses pharmaceutical compositions including a compound of formula II:

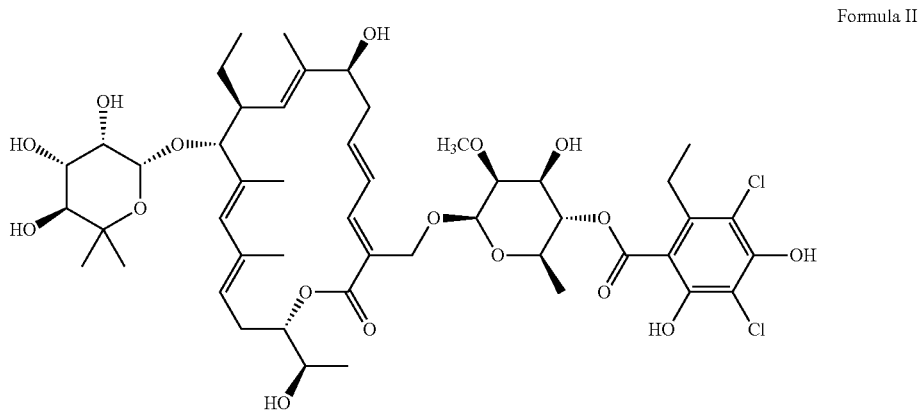 [SMILES: CCc1c(Cl)c(O)c(Cl)c(O)c1C(=O)O[C@H]1[C@H](O)[C@H](OC)[C@H](OC/C2=C\C=C\C[C@H](O)/C(C)=C/[C@H](CC)[C@@H](O[C@@H]3OC(C)(C)[C@@H](O)[C@H](O)[C@@H]3O)/C(C)=C/C(C)=C/C[C@@H]([C@@H](C)O)OC2=O)O[C@@H]1C]

Formula II in free form or in the form of its pharmaceutically acceptable salts.

In certain embodiments, the compound of Formula II is stereomerically pure.

In certain embodiments, the pharmaceutical composition is in the form of an oral dosage form.

In certain embodiments, the compound of Formula II is present in an amount of about 0.001 mg to about 4000 mg.

In certain embodiments, the oral dosage form is a tablet, capsule, gel cap, solution, syrup, or elixir.

In certain embodiments, the compound of Formula II is present in an amount of about 0.001 mg to about 2000 mg.

In certain embodiments, the compound of Formula II is present in an amount of about 0.01 mg to about 1000 mg.

In certain embodiments, the compound of Formula II is present in an amount of about 0.1 mg to about 800 mg.

In certain embodiments, the compound of Formula II is present in an amount of about 1 mg to about 500 mg.

In certain embodiments, the compound of Formula II is in the form of a hydrochloride salt.

In certain embodiments, the pharmaceutical composition further comprises a pharmaceutically acceptable carrier or vehicle.

The invention also encompasses methods for treating or preventing bacterial infections in a mammal, which comprises administering to said mammal a composition comprising a therapeutically or prophylactically effective amount of a compound of Formula II:

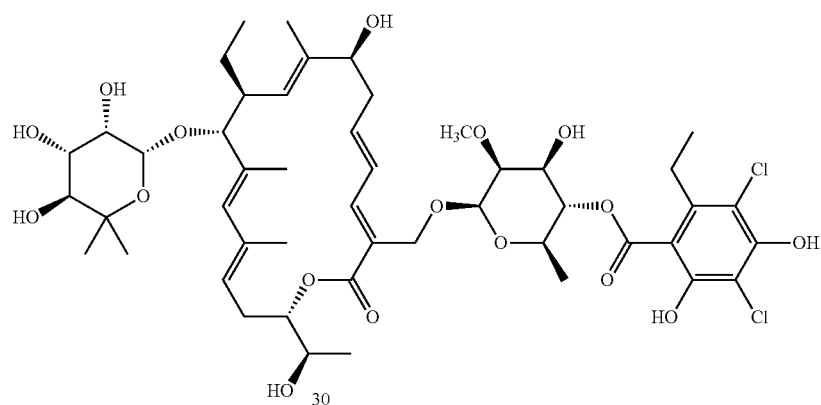

Formula II in free form or in the form of its pharmaceutically acceptable salts.

In certain embodiments, the therapeutically or prophylactically effective amount is from about 0.001 mg/kg to about 2000 mg/kg.

In certain embodiments, the mammal is human.

In certain embodiments, the route of administration is oral or parenteral.

In certain embodiments, the route of administration is intravenous, intradermal, intramuscular, intraperitoneal, subcutaneous, epidural, intracerebral, or intravaginal.

In certain embodiments, the dosage is 0.001 milligram to 200 milligrams per kilogram of the subject's body weight.

In certain embodiments, the dosage is 0.01 milligrams to 100 milligrams per kilogram of the subject's body weight.

In certain embodiments, the dosage is 0.1 milligrams to 50 milligrams per kilogram of the subject's body weight.

The invention also encompasses methods for treating or preventing bacterial infections in a mammal, which comprises contacting the gastrointestinal tract of said mammal with a compound of Formula II:

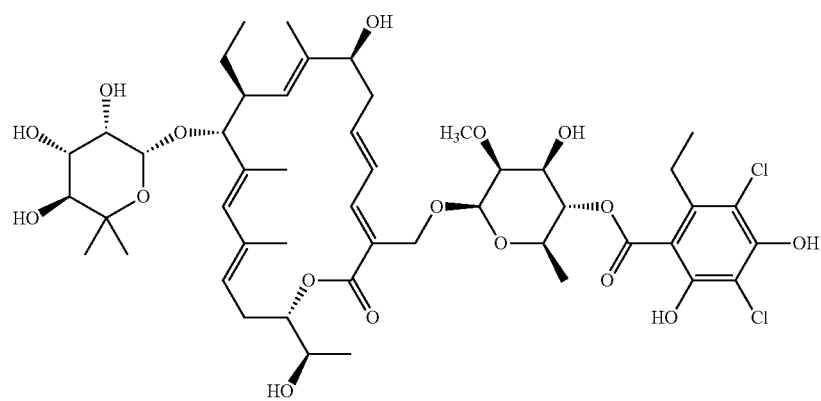

Formula II in free form or in the form of its pharmaceutically acceptable salts.

DEFINITIONS

As used herein, and unless otherwise indicated, the term "antibiotic-associated condition" refers to a condition resulting when antibiotic therapy disturbs the balance of the microbial flora of the gut, allowing pathogenic organisms such as enterotoxin producing strains of C. difficile, S. aureus and C. perfringens to flourish. These organisms can cause diarrhea, pseudomembranous colitis, and colitis and are manifested by diarrhea, urgency, abdominal cramps, tenesmus, and fever among other symptoms. Diarrhea, when severe, causes dehydration and the medical complications associated with dehydration.

As used herein, and unless otherwise indicated, the term "asymmetrically substituted" refers to a molecular structure in which an atom having four tetrahedral valences is attached to four different atoms or groups. The commonest cases involve the carbon atom. In such cases, two optical isomers (D- and L-enantiomers or R- and S-enantiomers) per carbon atom result which are nonsuperposable mirror images of each other. Many compounds have more than one asymmetric carbon. This results in the possibility of many optical isomers, the number being determined by the formula $2^n$, where n is the number of asymmetric carbons.

As used herein, and unless otherwise indicated, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, .alpha.-amino acid amides, alkoxyacyl amides, and alkylaminoalkylcarbonyl amides.

As used herein, and unless otherwise indicated, the term "broth" as used herein refers to the fluid culture medium as obtained during or after fermentation. Broth comprises a mixture of water, the desired antibiotic(s), unused nutrients, living or dead organisms, metabolic products, and the adsorbent with or without adsorbed product.

As used herein, and unless otherwise indicated, the term "compound" or "compounds of the invention" are used interchangeably and refer to a compound of Formula II, Formula IIa, salts, stereoisomers, mixtures of stereoisomers, and prodrugs thereof.

As used herein, and unless otherwise indicated, the term "excipient" refers to an inert substance added to a pharmacological composition to further facilitate administration of a compound. Examples of excipients include but are not limited to, calcium carbonate, calcium phosphate, various sugars and types of starch, cellulose derivatives, gelatin, vegetable oils and polyethylene glycols.

As used herein, and unless otherwise indicated, the term "halogen" includes F, Cl, Br and I.

As used herein, and unless otherwise indicated, the term "hydrate" means a compound of the present invention or a salt thereof that further includes a stoichiometric or non-stoichiometric amount of water bound by non-covalent intermolecular forces.

As used herein, and unless otherwise indicated, the term "isomeric mixture" means a mixture of two or more configurationally distinct chemical species having the same chemical formula. An isomeric mixture is a genus comprising individual isomeric species. Examples of isomeric mixtures include stereoisomers (enantiomers and diastereomers), regioisomers, as might result for example from a pericyclic reaction. The compounds of the present invention comprise asymmetrically substituted carbon atoms. Such asymmetrically substituted carbon atoms can result in mixtures of stereoisomers at a particular asymmetrically substituted carbon atom or a single stereoisomer. As a result, racemic mixtures, mixtures of diastereomers, as well as single diastereomers of the compounds of the invention are included in the present invention.

As used herein, and unless otherwise indicated, the term "lower alkyl," alone or in combination, refers to an optionally substituted straight-chain or optionally substituted branched-chain having from 1 to about 8 carbons (e.g., $C_1$, $C_2$, $C_3$, $C_4$, $C_5$, $C_6$, $C_7$, $C_8$,), more preferably 1 to 4 carbons (e.g., $C_1$, $C_2$, $C_3$, $C_4$,). Examples of alkyl radicals include methyl, ethyl, n-propyl, isopropyl, n-butyl, isobutyl, sec-butyl, tert-butyl. A "lower alkyl" is generally a shorter alkyl, e.g., one containing from 1 to about 4 carbon atoms (e.g., $C_1$, $C_2$, $C_3$, $C_4$,).

As used herein, and unless otherwise indicated, the term "macrocycles" refers to organic molecules with large ring structures usually containing over 10 atoms.

As used herein, and unless otherwise indicated, the term "18-membered macrocycles" refers to organic molecules with ring structures containing 18 atoms.

As used herein, and unless otherwise indicated, the term "membered ring" can embrace any cyclic structure, including carbocycles and heterocycles as described above. The term "membered" is meant to denote the number of skeletal atoms that constitute the ring. Thus, for example, pyridine, pyran and thiopyran are 6 membered rings and pyrrole, furan, and thiophene are 5 membered rings.

As used herein, and unless otherwise indicated, the term "MIC" or "minimum inhibitory concentration" refers to the lowest concentration of an antibiotic that is needed to inhibit growth of a bacterial isolate in vitro. A common method for determining the MIC of an antibiotic is to prepare several tubes containing serial dilutions of the antibiotic, that are then inoculated with the bacterial isolate of interest. The MIC of an antibiotic can be determined from the tube with the lowest concentration that shows no turbidity (no growth).

As used herein, and unless otherwise indicated, the term "MIC$_{50}$" refers to the lowest concentration of antibiotic required to inhibit the growth of 50% of the bacterial strains tested within a given bacterial species.

As used herein, and unless otherwise indicated, the term "MIC$_{90}$" refers to the lowest concentration of antibiotic required to inhibit the growth of 90% of the bacterial strains tested within a given bacterial species.

As used herein, and unless otherwise indicated, the term "OPT-80" refers to a preparation containing R-Tiacumicin B and Tiacumicin B related compounds (including, but not limited to, Tiacumicins, Lipiarmycin A4 and C-19 Ketone). Preparations of this type are described in detail in PCT application PCT/US03/21977, having an international publication number of WO 2004/014295 A2 and which preparations and are incorporated here by reference.

As used herein, and unless otherwise indicated, the term "pharmaceutically acceptable carrier" refers to a carrier or diluent that is pharmaceutically acceptable.

As used herein, and unless otherwise indicated, the term "pharmaceutically acceptable salts" refers to those derived from pharmaceutically acceptable inorganic and organic bases. Salts derived from appropriate bases include alkali metal (e.g., sodium or potassium), alkaline earth metal (e.g., magnesium), ammonium and N(C$_1$-C$_4$ alkyl)$_4^+$ salts, and the like. Illustrative examples of some of these include sodium hydroxide, potassium hydroxide, choline hydroxide, sodium carbonate, and the like. The term "pharmaceutically acceptable salt" also refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. Particularly preferred are hydrochloric, hydrobromic, phosphoric, and sulfuric acids, and most particularly preferred is the hydrochloride salt.

As used herein, and unless otherwise indicated, the term "pharmaceutical composition" refers to a composition of the R-Tiacumicin described herein, or physiologically acceptable salts thereof, with other chemical components, such as physiologically acceptable carriers and/or excipients. The purpose of a pharmaceutical composition is to facilitate administration of a compound to a mammal, including humans.

As used herein, and unless otherwise indicated, the term "physiologically acceptable carrier" is used synonymously with the term "pharmaceutically acceptable carrier" and refers to a carrier or diluent that does not cause significant irritation to an organism and does not abrogate the biological activity and properties of the administered compound.

As used herein, and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. When used to describe a compound of the invention, the term "prodrug" may also to be interpreted to exclude other compounds of the invention for example racemates.

As used herein, and unless otherwise indicated, the term "pseudomembranous colitis" or "enteritis" refers to the formation of pseudomembranous material (i.e., material composed of fibrin, mucous, necrotic epithelial cells and leukocytes) due to inflammation of the mucous membrane of both the small and large intestine.

As used herein, and unless otherwise indicated, the term "R" and "S" configuration, as used herein, are as defined by the IUPAC 1974 Recommendations for Section E, Fundamental Stereochemistry, *Pure Appl. Chem*. (1976) 45, 13-30. Chiral molecules can be named based on the atomic numbers of the atoms or groups of atoms, the ligands that are attached to the chiral center. The ligands are given a priority (the higher the atomic number the higher the priority) and if the priorities increase in a clockwise direction, they are said to be R-configuration. Otherwise, if they are prioritized in a counter-clockwise direction they are said to be S— configuration.

As used herein, and unless otherwise indicated, the term "R-Tiacumicin B" refers to the optically pure (R)-isomer of Tiacumicin B with an (R)-hydroxy group at C-19, as shown below:

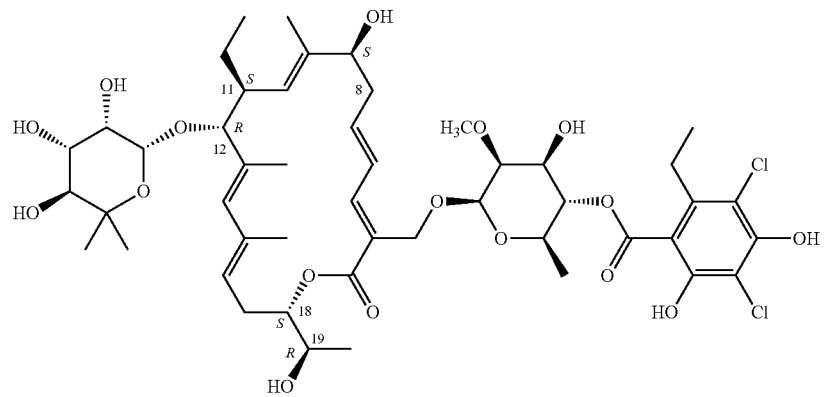

As used herein, and unless otherwise indicated, the term "stereoisomers" refers to compounds whose molecules have the same number and kind of atoms and the same atomic arrangement, but differ in their spatial arrangement.

As used herein, and unless otherwise indicated, the terms "optically pure," "stereomerically pure," and "substantially stereomerically pure" are used interchangeably and mean one stereoisomer of a compound or a composition that comprises one stereoisomer of a compound and is substantially free of other stereoisomer(s) of that compound. For example, a stereomerically pure compound or composition of a compound having one chiral center will be substantially free of the opposite enantiomer of the compound. A stereomerically pure compound or composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein, and unless otherwise indicated, the term "subject" refers to a human or animal in need of medical treatment. For the purposes of this invention, human subjects are typically institutionalized in a primary medical care facility such as a hospital or nursing home. However, treatment of a disease associated with the use of antibiotics or cancer chemotherapies or antiviral therapies can occur on an outpatient basis, upon discharge from a primary care facility, or can be prescribed by a physician for home-care, not in association with a primary medical care facility. Animals in need of medical treatment are typically in the care of a veterinarian.

As used herein, and unless otherwise indicated, the term "sugar" generally refers to mono-, di- or oligosaccharides. A saccharide may be substituted, for example, glucosamine, galactosamine, acetylglucose, acetylgalactose, N-acetylglucosamine, N-acetyl-galactosamine, galactosyl-N-acetylglucosamine, N-acetylneuraminic acid (sialic acid), etc., as well as sulfated and phosphorylated sugars. For the purposes of this definition, the saccharides are in their pyranose or furanose form.

As used herein, and unless otherwise indicated, the term "Tiacumicin" as used herein refers to a family of compounds all of which comprise the 18-membered macrocycle shown below in Formula I:

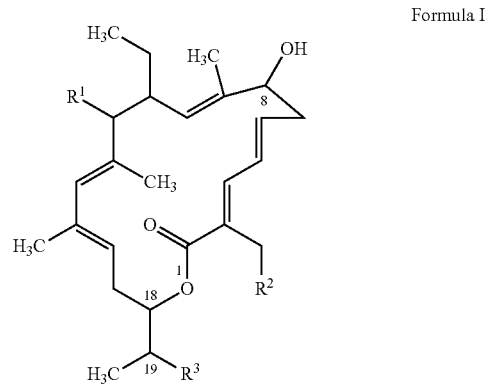

Formula I

As used herein, and unless otherwise indicated, the term "yield" as used herein refers to an amount of crude Tiacumicin re-constituted in methanol to the same volume as the original fermentation broth. Yield is determined using standard HPLC techniques. Yield is reported in units of mg/L.

Compound of the Invention

The compound of the invention is a metabolite of Tiacumicin B having the structure of Formula II, wherein the isopropylcarboxy group on the sugar of Tiacumicin B has been cleaved:

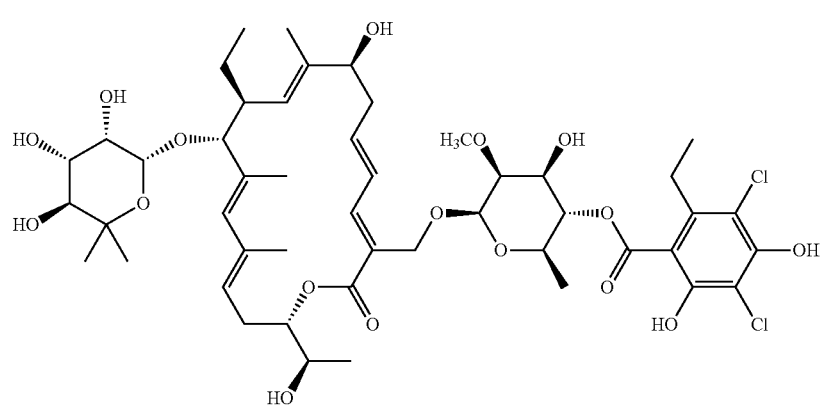

Formula II

This invention relates to a pharmaceutical compound of Formula II in free form or in the form of its pharmaceutically acceptable salts.

In certain embodiments, the compound of the invention is a metabolite of R-Tiacumicin B, (i.e., the compound of Formula II).

In certain embodiments, the compound of Formula II is racemic and can be represented by the compound of Formula IIa.

Formula IIa

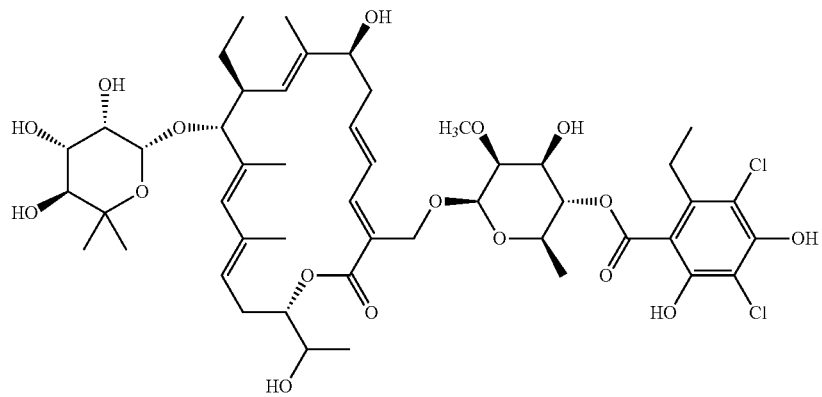

In other embodiments, the compound of Formula II is substantially stereomerically pure and can be illustrated by the compound of Formula II.

The invention also encompasses pharmaceutically acceptable salts of the metabolite of tiacumicin B.

Therapeutic and Prophylactic Uses of the Compound of the Invention

The invention encompasses a compound of Formula II that is effective in treating disorders associated with bacterial infections, specifically GI infections caused by toxin producing strains of Clostridium difficile (C. difficile) and Clostridium perfringens (C. perfringens).

In another embodiment of the invention is the selective effect of the compound of Formula II on C. difficile similar to that of the parent compound, OPT-80, and was as active as vancomycin against C. difficile.

In other embodiments, the invention encompasses methods of treating antibiotic-associated conditions including administering a therapeutically effective amount of a compound of Formula II or Formula IIa or a salt thereof or a composition comprising such compound to a subject in need thereof.

In other embodiments, the invention encompasses methods of treating a condition resulting when antibiotic therapy disturbs the balance of the microbial flora of the gut, allowing pathogenic organisms such as enterotoxin producing strains of C. difficile, S. aureus and C. perfringens to flourish. The method includes administering a therapeutically effective amount of a compound of Formula II or Formula IIa or a salt thereof or a composition comprising such compound to a subject in need thereof.

In other embodiments, the invention encompasses methods of treating disorders associated with the abnormal growth of C. difficile, S. aureus and C. perfringens in the intestinal tract and in certain embodiments in a subject taking antibiotics or other antimicrobial drugs. Disorders that can be treated or prevented by the present methods include symptoms ranging from diarrhea to life-threatening inflammations of the colon, and include, but are not limited to, pseudomembranous colitis—severe inflammations of the colon, and colitis manifested by diarrhea, urgency, abdominal cramps, tenesmus, and fever among other symptoms. Diarrhea, when severe, causes dehydration and the medical complications associated with dehydration.

Further disorders associated with C. difficile, S. aureus and C. perfringens that can be treated with a compound of Formula II or a compound of Formula IIa or a salt thereof or a composition comprising such a compound include, but are not limited to, bouts of watery diarrhea, often with nausea and abdominal pain and cramping, colitis or pseudomembranous colitis, profuse watery diarrhea—10 or more bowel movements a day, fever, often greater than 101° F., abdominal pain, which may be severe, blood or pus in the stool, nausea, dehydration, and weight loss In certain embodiments, subjects can develop C. difficile, S. aureus and C. perfringens infections during or shortly after a course of antibiotics, but signs and symptoms may not appear for weeks or even months after treatment has stopped. The compounds and composition of the invention are useful for long-term treatment and to prevent the recurrence of a bacterial infection or a disorder associated with a bacterial infection.

Without being limited by theory, it is believed that when a subject takes an antibiotic to treat an infection, it often destroys these beneficial bacteria as well as the bacteria that are causing the illness. Without enough healthy bacteria, dangerous pathogens such as C. difficile can quickly grow out of control. Once C. difficile takes hold it can produce virulent toxins that attack the lining of the intestine. The toxins destroy cells and produce pseudomembranes—telltale patches (plaques) of inflammatory cells and decaying cellular debris on the interior surface of the colon. Without being limited by theory, it is believed that almost any antibiotic can cause harmful bacteria to proliferate in the intestine, but ampicillin, amoxicillin, clindamycin, fluoroquinolones and cephalosporins are most often implicated in C. difficile infections. The use of broad-spectrum drugs that target a wide range of bacteria and the taking of antibiotics for a prolonged period increase the chance of infection. Other antimicrobials, including antiviral and antifungal drugs and chemotherapy medications also can lead to an increased risk of infection with C. difficile.

Accordingly, the invention further encompasses compositions and formulations comprising a compound of formula II or a salt thereof that are useful in treating infection, for example a bacterial infection, caused by abnormal growth of *C. difficile, S. aureus* and *C. perfringens* and/or treating or preventing disorders associated with abnormal growth of *C. difficile, S. aureus* and *C. perfringens*.

The invention also encompasses methods of treating infection, for example a bacterial infection, including but not limited to, a bacterial infection caused by *C. difficile, S. aureus* and *C. perfringens* and/or treating or preventing disorders associated with *C. difficile, S. aureus* and *C. perfringens* comprising administering to a subject, preferably to a mammal in need of said treatment or prevention a therapeutically or prophylactically effective amount of a compound of Formula II or Formula IIa or a salt thereof or a composition including such a compound.

In one embodiment, a composition of the invention comprising a compound of Formula II or Formula IIa or a salt thereof and a pharmaceutically acceptable vehicle, is administered to a mammal, preferably a human, with a disorder associated with anaerobic and microaerophilic GI flora.

In another embodiment, a composition of the invention comprising a compound of Formula II or Formula IIa or a salt thereof and a pharmaceutically acceptable vehicle, is administered to a mammal, preferably a human, with an infection caused by *C. difficile, S. aureus* and *C. perfringens*.

In another embodiment, a composition of the invention comprising a compound of Formula II or Formula IIa or a salt thereof and a pharmaceutically acceptable vehicle, is administered to a mammal, preferably a human, with a *C. difficile, S. aureus* and/or *C. perfringens* associated disorder.

In one embodiment, "treatment" or "treating" refers to an amelioration of a disease or disorder, or at least one discernible symptom thereof, associated with a bacterial infection associated with abnormal growth of anaerobic and microaerophilic GI flora or *C. difficile, S. aureus* and *C. perfringens*. In another embodiment, "treatment" or "treating" refers to an amelioration of at least one measurable physical parameter, not necessarily discernible by the subject in need of the treatment. In yet another embodiment, "treatment" or "treating" refers to inhibiting the progression of a disease or disorder, either physically, for example, stabilization of a discernible symptom, physiologically, for example, stabilization of a physical parameter, or both. In yet another embodiment, "treatment" or "treating" refers to delaying the onset of a disease or disorder.

In certain embodiments, the compositions of the invention are administered to a subject, preferably a human, as a preventative measure against such diseases. As used herein, "prevention" or "preventing" refers to a reduction of the risk of acquiring a given disease or disorder. In a preferred mode of the embodiment, the compositions of the invention are administered as a preventative measure to a subject, preferably a human having a predisposition to a bacterial infection or disorder associated with abnormal growth of anaerobic and microaerophilic GI flora or *C. difficile, S. aureus* and/or *C. perfringens*.

Therapeutic/Prophylactic Administration and Compositions

Due to the activity of the compounds of Formula II and Formula IIa and salts thereof, the compounds are advantageously useful in veterinary and human medicine. As described above, the compounds of the invention are useful for the treatment or prevention of a disorder associated with anaerobic and microaerophilic GI flora, *C. difficile*, or a disorder associated with *C. difficile, S. aureus* and/or *C. perfringens*.

In some embodiments, the subject has abnormal/altered gut flora but does not exhibit or manifest any physiological symptoms associated with abnormal growth of anaerobic and microaerophilic GI flora, *C. difficile, S. aureus* and/or *C. perfringens*, or a disorder associated with *C. difficile, S. aureus* and/or *C. perfringens*.

The invention encompasses methods of treatment and prophylaxis by administration to a subject of a therapeutically or prophylactically effective amount of a composition comprising a compound of Formula II. The invention also encompasses methods of treatment and prophylaxis by contacting the gut or GI tract of a subject with a therapeutically or prophylactically effective amount of a compound of Formula II or Formula IIa or a salt thereof.

The subject is a mammal, including, but not limited, to an animal such a cow, horse, sheep, pig, chicken, turkey, quail, cat, dog, mouse, rat, rabbit, guinea pig, and is more preferably a human.

The compositions, which comprise a compound of Formula II, are preferably administered orally. The compounds of the invention may also be administered by any other convenient route, for example, by infusion or bolus injection, by absorption through epithelial or mucocutaneous linings (e.g., oral mucosa, rectal and intestinal mucosa) and may be administered together with another biologically active agent. Administration can be systemic or local. Various delivery systems are known, for example, encapsulation in liposomes, microparticles, microcapsules, capsules, etc., and can be used to administer a compound of formula II, Formula IIa, or a salt thereof. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition.

In most instances, administration will not result in the release of the compounds of the invention into the bloodstream. For example, in accordance with one embodiment of the invention, after multiple dose oral administrations, low MCC levels of Formula II were detected in plasma, most of which fell below the limit of quantification. By contrast, fecal levels of Formula II in the studies were extremely high, exceeding 1,000 times its MIC values versus *C. difficile*.

However, in certain embodiments in may be useful to administer the compounds of the invention systemically. Accordingly, in other embodiments, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, for example, in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue.

Pulmonary administration can also be employed, for example, by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of the target of the compounds of the invention, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used.

The compositions will contain a therapeutically or prophylactically effective amount of a compound of Formula II, Formula IIa or a salt thereof, preferably in purified form, together with a suitable amount of a pharmaceutically acceptable vehicle to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compounds of the invention can also be administered in the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule. (See e.g., U.S. Pat. No. 5,698,155). Other examples of suitable pharmaceutical vehicles are described in "Remington's Pharmaceutical Sciences" by A. R. Gennaro.

In a certain embodiment, the compounds of Formula II are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

In other embodiments, the compositions of the invention can be administered orally. Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances.

Suitable amounts of the compound of Formula II or IIa or a salt thereof in an oral composition for oral administration are generally about 0.001 milligram to 4000 milligrams of a compound of the invention. In preferred embodiments of the invention, the amount is about 0.01 milligram to 2000 milligrams, more preferably about 0.1 milligram to 1000 milligrams, more preferably 0.5 milligram to 800 milligrams, and yet more preferably 1 milligram to 500 milligrams. In a preferred embodiment, the amount of compound of the invention or a salt thereof in the composition is about 4000 milligrams of a compound. In a preferred embodiment, the amount of compound of the invention or a salt thereof in the composition is about 2000 milligrams of a compound. In a preferred embodiment, the amount of compound of the invention or a salt thereof in the composition is about 1000 milligrams of a compound. In a preferred embodiment, the amount of compound of the invention or a salt thereof in the composition is about 500 milligrams of a compound. In another preferred embodiment, the amount of compound of the invention or a salt thereof in the composition is about 250 milligrams of a compound. In a preferred embodiment, the amount of compound of the invention or a salt thereof in the composition is about, 100 milligrams of a compound. In a preferred embodiment, the amount of compound of the invention or a salt thereof in the composition is about 50 milligrams of a compound. In a preferred embodiment, the amount of compound of the invention or a salt thereof in the composition is about 10 milligrams of a compound. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight. In certain embodiments, the oral dosage regimen can include taking multiple oral dosages in a single day, for example, taking the oral dose once a day, twice a day, three times a day, four times a day or more spaced out throughout the day.

In other embodiments, suitable dosage ranges for oral administration can be generally about 0.001 milligram to 2000 milligrams of a compound of the invention per kilogram body weight. In specific preferred embodiments of the invention, the oral dose is 0.01 milligram to 1000 milligrams per kilogram body weight, more preferably 0.1 milligram to 500 milligrams per kilogram body weight, more preferably 0.5 milligram to 200 milligrams per kilogram body weight, and yet more preferably 1 milligram to 100 milligrams per kilogram body weight. In a most preferred embodiment, the oral dose is 5 milligrams of a compound of the invention per kilogram body weight. The dosage amounts described herein refer to total amounts administered; that is, if more than one compound of the invention is administered, the preferred dosages correspond to the total amount of the compounds of the invention administered. Oral compositions preferably contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. The compounds of the invention can also be incorporated into a topical formulation, for example, an ointment, suave, cream, or oil. Suitable doses of the compounds of the invention for topical administration are in the range of 0.001 milligram to 2000 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. Other methods will be known to the skilled artisan and are within the scope of the invention.

EXAMPLES

The following examples are provided by way of describing specific embodiments of the present invention without intending to limit the scope of the invention in any way.

Example 1

Formula II Preparation

At 0° C., LiOH (42 mg) in 12 mL of MeOH was added to 783 mg of OPT-80. The Solution was kept at 0° C. for 5 h, and then quenched by addition of saturated $NH_4Cl$ solution. The resulting mixture was extracted with chloroform. The organic layer was separated, dried and concentrated. The crude was purified by silica gel column chromatography with $CH_2Cl_2$: $CH_3OH$ 10:1 as eluents. The desired product (154 mg) was isolated with 97.05% purity by HPLC.

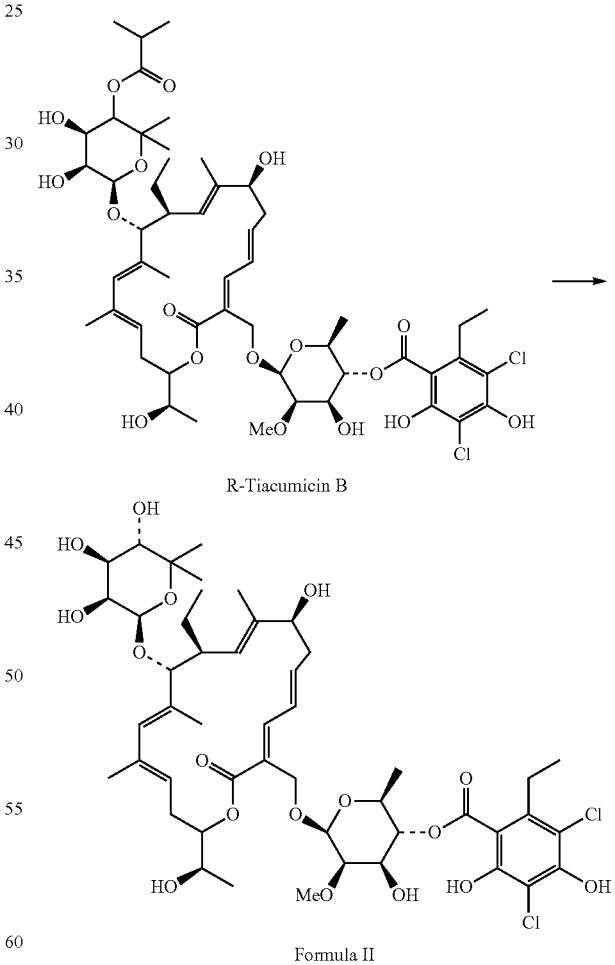

Formula II

Analytical data of Formula II.
MS m/z (ESI) 1004.4 $(M+NH_4)^+$;
$^1H$ NMR (400 MHz, $CDCl_3$) δ 7.12 (d, J=11.4 Hz, 1H), 6.59 (dd, J=14.7, 11.4 Hz, 1H), 5.85 (br s, 1H), 5.83 (ddd, J=14.7, 10.6, 4.0 Hz, 1H), 5.47 (dd, J=8.1, 7.6 Hz, 1H), 5.15 (dd, J=9.6, 9.6 Hz, 1H), 4.98 (d, J=10.6 Hz, 1H), 4.76-4.70

(m, 1H), 4.69 (d, J=11.6 Hz, 1H), 4.63 (br s, 1H), 4.62 (br s, 1H), 4.39 (d, J=11.6 Hz, 1H), 4.29-4.23 (m, 1H), 4.07-3.98 (m, 2H), 3.72-3.48 (m, 5H), 3.62 (s, 3H), 3.17 (d, J=5.8 Hz, 1H), 3.14-2.96 (m, 2H), 2.81-2.45 (m, 5H), 2.33-2.25 (m, 1H), 1.92 (s, 3H), 1.81 (s, 3H), 1.67 (s, 3H), 1.64-1.57 (m, 1H), 1.34 (d, J=6.1 Hz, 3H), 1.27 (s, 3H), 1.21 (t, J=7.3 Hz, 3H), 1.19 (d, J=6.8 Hz, 3H), 1.05 (s, 3H), 0.83 (t, J=7.3 Hz, 3H);

$^{13}$C NMR (100 MHz, CDCl$_3$) δ 170.1, 168.9, 157.6, 152.7, 144.2, 140.9, 140.5, 136.9, 136.3, 134.5, 134.4, 129.1, 127.9, 125.3, 123.3, 113.9, 107.6, 107.2, 101.9, 94.6, 92.4, 82.3, 78.2, 76.9, 74.6, 74.5, 72.7, 71.9, 71.8, 71.4, 70.1, 69.2, 63.7, 62.3, 41.9, 36.9, 28.9, 28.4, 26.2, 25.9, 18.5, 17.8, 17.4, 17.2, 15.5, 14.1, 13.9, 11.2. Aqueous solubility: ~300 mg/mL HPLC Chromatography analysis was performed using Walters 2695 separation module, with Walters 2487 detector.

Column: Agilent, ZORBAX Eclipse XDB-C8 4.6×150 mm 3.5 micron

Detector wavelength: 230 nm

Mobile phase A is water, 0.1% TFA, mobile phase B is acetonitrile 0.05% TFA

Gradient:

| Time (min) | Flow (ml/min) | A | B |
| --- | --- | --- | --- |
|  | 1 | 60 | 40 |
| 3 | 1 | 50 | 50 |
| 14 | 1 | 39 | 61 |
| 14.5 | 1 | 60 | 40 |
| 19 | 1 | 60 | 40 |

Formula II came out at 4.81 min.

The 4.81 min peak was also found in the HPLC diagram of the crude material of OPT-80 production after fermentation.

Example 2

Formula II Biological Activity

Bacterial Strains:

Most bacterial strains were purchased from American Type Culture Collection (Manassas, Va.). A few clinical isolates of *Staphylococcus* and vancomycin resistant Enterococci were purchased from Christiana Care Health System (Wilmington, Del.) and were identified by Biomerieux API identification system (Durham, N.C.).

Antimicrobial Compounds:

OPT-80 and Formula II were produced by Optimer Pharmaceuticals. Vancomycin was purchased from Sigma-Aldrich (St. Louis, Mo.).

Formula II Profiling

The MIC of OPT-80 and its major metabolite, Formula II, against anaerobic and aerobic GI bacteria was determined using the CLSI standard susceptibility testing methods.

Agar Dilution Method: (1)

This method was used for anaerobic organisms (*Bacteroides, Clostridium, Bifidiobacteria, Prevotella, Fusobacterium, Peptococcus, Peptostreptococcus, Veillonella*) and microaerophilic *Lactobacillus* spp, all of which were purchased form American Type Culture Collection (ATCC):

1. Two fold dilutions of compounds were made in *Brucella* agar supplemented with hemin, vitamin K and 5% laked sheep blood to achieve a final concentration range from 0.016 µg/mL to 16 µg/mL.

2. Using the direct colony suspension method, bacterial inocula were prepared with densities close to a 0.5 McFarland standard (~$10^8$ CFU/mL), followed by spotting of the inocula onto agar plates using a Steers replicator to deliver ~$10^5$ CFU/spot.

3. Plates were incubated in an anaerobic chamber at 35° C. for 48 hours. For the *Lactobacillus* strains, Mueller Hinton Agar and an incubation atmosphere of 5% $CO_2$ were used.

4. The lowest concentration of an antibiotic showing no growth or marked reduction in growth was read as the MIC.

Microbroth Dilution Method:

This susceptibility method was used for aerobic and facultative organisms (*Escherichia, Pseudomonas, Salmonella, Haemophilus. Streptococcus, Staphylococcus* and *Enterococcus*):

1. Two fold serial dilutions of compounds were made in cation-adjusted Mueller Hinton broth to achieve a concentration range from 0.125 µg/mL to 64 µg/mL.

2. Using the direct colony suspension method, bacterial inocula at 0.5 McFarland standard were diluted and inoculated into each microtiter plate to a final density of approximately $5 \times 10^5$ CFU/mL (or $5 \times 10^4$ CFU/well).

3. The microtiter plates were incubated for 16-24 hours (depending on the organism) at 35° C. in ambient air.

4. The MIC was read as the lowest concentration at which there was no visible growth.

Effect of Fecal Material on the In Vitro Activity of OPT-80 and Formula II:

The in vitro activity of OPT-80, Formula II, and vancomycin against *C. difficile* ATCC 700057 was measured in the presence and absence of feces using microbroth dilution susceptibility testing methods according to the CLSI guidelines as is recommended for the *B. fragilis*. The Brucella broth media (BB) used for the experiment was supplemented with hemin (5 µg/mL) and vitamin K (1). The fecal slurry was prepared according to the method described by Swanson et al (Antimicrobial Agents and Chemotherapy. 35(6): 1108-1111; J of Antibiotics. XLII (1): 94-101).

1. Briefly, a 5% fecal slurry was prepared by adding 5.5 gram of fresh human fecal sample into 110 ml BB, followed by homogenization for approximately 10 minutes.

2. The slurry was aliquoted into separate tubes containing 2× the desired top concentrations of the following drugs: OPT-80, Formula II, vancomycin (VAN), or no drug (Preparations A-F and I, respectively).

3. Similar preparations of the above drugs in BB without feces were also prepared as controls for the experimental procedure (Preparations E-G and J, respectively).

Preparation A: Feces-supplemented BB+32 µg/mL OPT-80

Preparation B: Feces-supplemented BB+256 µg/mL Formula II

Preparation C: Feces-supplemented BB+256 µg/mL VAN

Preparation E: Unsupplemented BB+32 µg/mL OPT-80

Preparation F: Unsupplemented BB+256 µg/mL Formula II

Preparation G: Unsupplemented BB+256 µg/mL VAN

Preparation I: Feces-Supplemented Bb, Drug-Free

Preparation J: Unsupplemented BB, drug-free

Following 30 minutes incubation at room temperature, all preparations were centrifuged to remove solid material, filtered once through a 1.2 µm microfiber glass pre-filter, and filtered three times through 0.2 µm filter devices.

The filtrate materials from preparations A-C were serially diluted across the length of 96-well microtiter plates using the 5% fecal slurry filtrate (i.e. Preparation I) as the diluent.

The filtrate materials from Preparation E-G were serially diluted across the length of 96 well microtiter plates using BB (Preparation J) as the diluent.

The plates were transferred to an anaerobic glove box and were allowed to equilibrate for 4 hours to the anaerobic environment.

Bacterial inocula were prepared by harvesting bacteria from overnight culture and preparing a 0.5 McFarland suspension into feces-supplemented or unsupplemented BB.

Prepared inocula were then added to plates containing serially diluted drugs, resulting in a 1:2 dilution of drugs to give the desired final concentration.

The microtiter plates were incubated for ~48 hours at 35° C. under anaerobic conditions, and the MIC was read as the lowest drug concentration at which there was no visible growth.

Results of Formula II Profiling

Formula II, similar to the parent compound, demonstrated antimicrobial activity against some gram positive bacteria (including *C. difficile, C. perfringenes, B. longum, F. magna, P. asaccharolyticus, P. anaerobius, M. micros* and the microaerophilic *L. casei*), albeit with MIC values that were four to sixteen fold greater than those of OPT-80. With regards to other gram positive organisms such as *S. aureus, E. faecium* and *L. rhamnosus*, Formula II demonstrated in vitro activity with MICs of >16 µg/mL. This clearly demonstrates Formula II can be used as a very narrow spectrum antibiotic against *C. difficile*.

In the phase 2A study of OPT-80 in CDAD patients who were administered OPT-80 at 200 mg bid (the intended dosing regimen), fecal levels of the parent OPT-80 were 1433±975 µg/g, while fecal levels of the metabolite Formula II were 760±373 µg/g (6). Thus, after oral administration, both parent and metabolite are present at levels far in excess of their MIC values versus *C. difficile* (FIG. 1).

Formula II is present in the gut after oral dosing with OPT-80 at levels far in excess (1,000 times) of their MIC values vs. *C. difficile*.

TABLE 2

MIC data for OPT-80 and Formula II for a panel of aerobic bacteria

| | Aerobic Panel MIC (µg/mL) | | | | | | |
|---|---|---|---|---|---|---|---|
| Compound | ORG 83 E. faecalis ATCC 29212 | ORG 84 E. faecium ATCC 700221 VRE | ORG 85 E. faecium ATCC 19434 | ORG 97 S. aureus (MRSA) ATCC 33591 | ORG 98 S. aureus (MSSA) ATCC 29213 | ORG 99 S. epidermidis ATCC 12228 | ORG 101 S. pyogenes ATCC 19615 |
| OPT-80 | 2-4 | 4 | 8 | 8 | 8 | 4 | 16-32 |
| Formula II | 16-64 | >32 | >64 | >64 | >64 | >32 | >32 |

TABLE 1

Raw MIC data (µg/mL) for OPT-80 and Formula II against gram positive bacterial strains representative of GI flora.

| Gram Positive Organisms | Formula II | OPT-80 |
|---|---|---|
| *Bifidiobacterium longum*, ATCC 15707 | 1 | 0.125 |
| *Clostridium difficile*, ATCC 700057 | 2 | 0.25 |
| *Clostridium difficile*, ATCC 43255 | 4 | 0.5 |
| *Clostridium perfringens*, ATCC 13124 | 1 | 0.125 |
| *Enterococcus faecium*, ATCC 19434 | >64 | 4 |
| *Enterococcus faecium*, Vancomycin resistant clinical strain ORG#360 | >64 | 8 |
| *Enterococcus faecium*, Vancomycin resistant clinical strain ORG#364 | 64 | 2 |
| *Enterococcus faecium*, Vancomycin resistant clinical strain ORG#534 | >64 | 4 |
| *Finegoldia* (formerly *Peptococcus*) *magna*, ATCC 29328 | 8 | 1 |
| *Lactobacillus. casei*, ATCC 393 | 8 | 2 |
| *Lactobacillus acidophilus*, ATCC 4356 | >16 | >16 |
| *Lactobacillus rhamnosus*, ATCC 7496 | >16 | 8 |
| *Micromonas* (formerly *Peptostreptococcus*) *micros*, ATCC 33270 | 1 | 0.125 |
| *Peptoniphilus* (formerly *Peptococcus*) *asaccharolyticus*, ATCC 29743 | 4 | 1 |
| *Peptostreptococcus anaerobius*, ATCC 27337 | 0.25 | 0.016 |
| *Staphylococcus aureus*, ATCC 29213 | >64 | 8 |
| *Staphylococcus aureus*, ATCC 33591 (Methicilin resistant) | >64 | 4 |
| *Staphylococcus aureus*, Methicilin resistant clinical strain ORG#578 | >64 | 8 |
| *Staphylococcus epidermidis*, clinical strain ORG#365 | 64 | 4 |
| *Streptococcus pneumoniae*, ATCC 49619 | >64 | 64 |
| *Streptococcus pyogenes*, ATCC 19615 | >64 | 16 |

TABLE 3

MIC data for OPT-80 and Formula II for a panel of anaerobic bacteria Aerobic Panel MIC (µg/mL)

| Compound | ORG 830 *C. difficile* ATCC 700057 | ORG 150 *B. fragilis* 25285 |
|---|---|---|
| OPT-80 | 0.030, 0.06 | >16 |
| Formula II | 0.5-1 | >16 |

Effect of Fecal Material on In Vitro Activity of OPT-80 and Formula II:

The effect of fecal material on the antimicrobial activity of OPT-80, Formula II and vancomycin, which is the only FDA approved treatment for CDAD, was evaluated vs. *C. difficile* ATCC strain 700057 (Table 3).

In the presence of 5% fecal material, a similar fold increase in MIC values was observed for all three drugs; OPT-80 (2 µg/ml; eight fold), Formula II (4 µg/ml; four fold) and vancomycin (8 µg/ml; four fold). The in vitro data demonstrates that even in the presence of fecal material both the metabolite and OPT-80 have better or similar in vitro activity compared to vancomycin, the approved treatment for CDAD. Furthermore, the average fecal concentration of OPT-80 following oral administration has been shown to be over 1,400 µg/g of stool (6), a level far in excess of the MIC even in the presence of fecal material.

TABLE 4

In vitro activity of drugs in presence or absence of fecal material vs. *C. difficile* ATCC strain 700057

| | MIC (µg/mL) | | |
|---|---|---|---|
| Diluent | OPT-80 | FORMULA II | Vancomycin |
| Brucella broth only | 0.25 | 1 | 2 |
| Brucella broth with feces | 2 | 4 | 8 |
| Fold increase in MIC | 8x | 4x | 4x |

All references discussed above are herein incorporated by reference in their entirety for all purposes. While this invention has been particularly shown and described with refer-

What is claimed is:

1. An isolated compound of Formula II

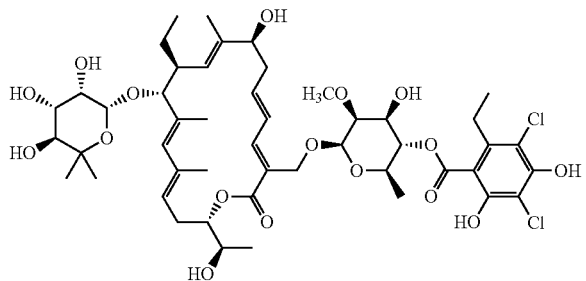

Formula II in free form or in the form of its pharmaceutically acceptable salt.

2. The isolated compound of claim 1, wherein the compound of Formula II is greater than 80% by weight stereomerically pure.

3. The isolated compound of claim 1, wherein the compound of Formula II is an alkaline metal or tertiary alkyl ammonium salt.

4. The isolated compound of claim 1, wherein the compound of Formula II is a $Na^+$, $K^+$, $Mg^{2+}$, $Ca^{2+}$, $Zn^{2+}$ salt.

5. The isolated compound of claim 1, wherein the compound of Formula II is greater than 90% by weight stereomerically pure.

6. The isolated compound of claim 1, wherein the compound of Formula II is greater than 95% by weight stereomerically pure.

7. The isolated compound of claim 1, wherein the compound of Formula II is greater than 97% by weight stereomerically pure.

8. The isolated compound of claim 1, wherein the compound of Formula II is substantially free of other diastereomers of the compound.

* * * * *